Figure 1:
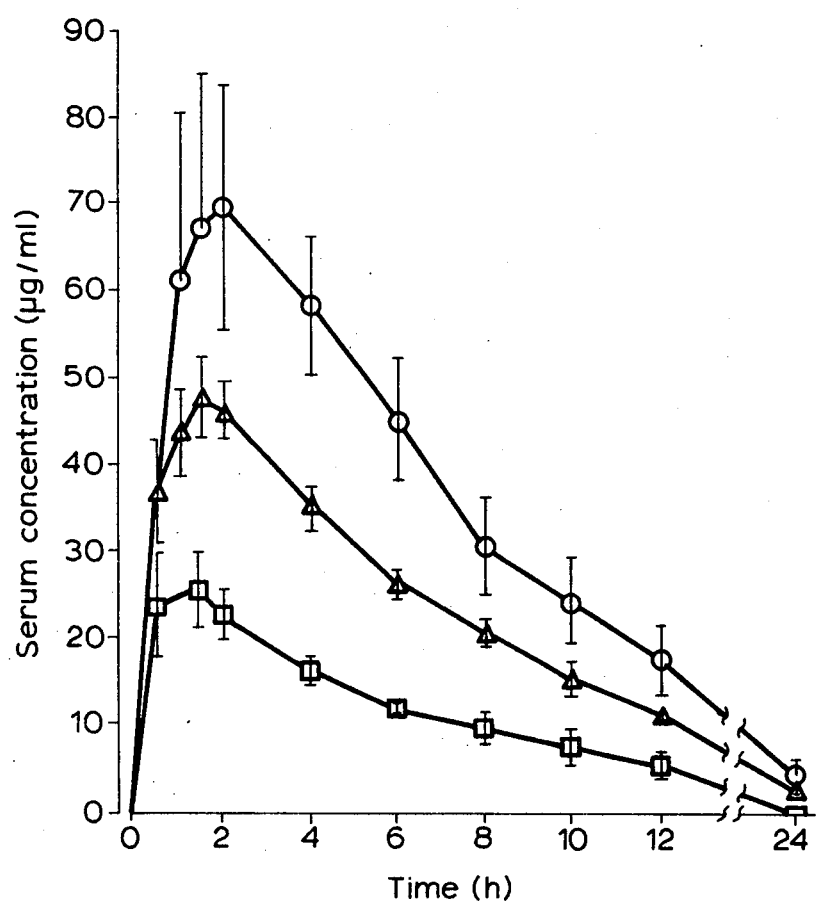

United States Patent [19]

Sutherland et al.

[11] Patent Number: 4,481,210

[45] Date of Patent: Nov. 6, 1984

[54] METHOD OF TREATMENT

[75] Inventors: Robert Sutherland, Dorking; Brian Slocombe, Ewhurst, both of England

[73] Assignee: Beecham Group p.l.c., England

[21] Appl. No.: 363,487

[22] Filed: Mar. 30, 1982

[30] Foreign Application Priority Data

Apr. 15, 1981 [GB] United Kingdom ............ 8111939

[51] Int. Cl.³ .................................... A61K 31/43
[52] U.S. Cl. .......................................... 424/271
[58] Field of Search ................................ 424/271

[56] References Cited

FOREIGN PATENT DOCUMENTS 1538051 1/1979 United Kingdom .
1538052 1/1979 United Kingdom .

OTHER PUBLICATIONS

1982 Physician's Desk Reference, 36th Edition, pp. 1403, 1404, 415.

Primary Examiner—Jerome D. Goldberg
Attorney, Agent, or Firm—Jacobs & Jacobs

[57] ABSTRACT

A method of treatment of bacterial infections in humans which comprises administering to a patient one or two unit dosages per day of a compound of formula (I):

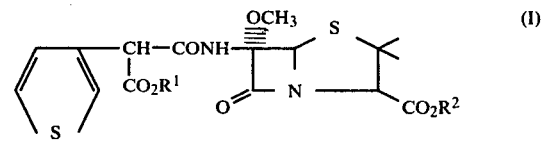

wherein
$R^1$ is hydrogen, a pharmaceutically acceptable salting ion or a pharmaceutically acceptable ester-forming radical, and
$R^2$ is hydrogen, a pharmaceutically acceptable salting ion or an in vivo hydrolyzable ester-forming radical.

4 Claims, 3 Drawing Figures

METHOD OF TREATMENT

This invention relates to a method of treatment employing compounds having pharmaceutical activity and to the unit dosage composition used therein. More specifically this invention relates to the treatment of bacterial infection with a penicillin derivative and to the unit dosage composition used therein.

U.K. Pat. Nos. 1538051 and 1538052 disclose inter alia the compounds of formula (I):

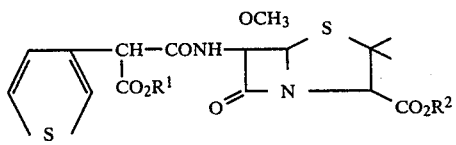

wherein
$R^1$ is hydrogen, a pharmaceutically acceptable salting ion or a pharmaceutically acceptable ester-forming radical, and
$R^2$ is hydrogen, a pharmaceutically acceptable salting ion or an in vivo hydrolysable ester-forming radical.

U.K. Pat. Nos. 1538051 and 1538052 further disclose pharmaceutical compositions comprising a compound of formula (I) above together with a pharmaceutical carrier or excipient.

We have now found that the compounds of formula (I) are exceptional in producing high and prolonged serum concentrations when administered to man.

Accordingly the present invention provides a method of treatment of bacterial infections in humans which comprises administering to a patient one or two unit dosages per day of a compound of formula (I). Preferably the administration comprises a single unit dosage per day.

The compositions may be formulated for administration by any route, although parenteral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol, or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oil suspensions, solutions, emulsions, syrups, or elixirs, or may be presented as dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; nonaqueous vehicles (which may include edible oils), for example almond oil, fractionated coconut oil, oily esters such as glycerine, porpylene glycol, or ethyl alcohol; preservatives, for example methyl or propyl p-hydroxybenzoate or sorbic acid, and if desired convention flavouring or colouring agents.

Suppositories will contain conventional suppository bases, e.g. cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The unexpected properties of the compounds (I) enable a therapeutically effective level of compound to be present in the blood stream over a period of 24 hrs.

The dosage as employed for adult human treatment will suitably range from 500 to 3000 mg per unit dose, preferably the dosage will be in the range from 750 to 1250 mg per unit dose, with a unit dose of 1000 mg being a convenient standard dosage unit. The dosage will depend on the route of administration of the composition; however for administration by intravenous or intramuscular injection a unit dose of 1000 mg is particularly preferred.

The present invention further provides a pharmaceutical container comprising unit dosages of a compound of formula (I), said container being associated with an indication to administer one or two unit dosages per day.

The dosage units administered according to the method of the invention do not require any sustained release formulations to maintain the high and prolonged serum concentrations of compound (I).

One preferred embodiment of the present invention provides a method of treatment of bacterial infections in humans which comprises administering to a patient one or two unit doses per day of a compound of formula (II):

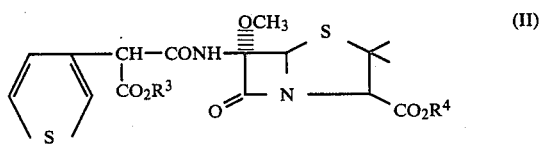

wherein $R^3$ and $R^4$ may be the same or different and each represents hydrogen or a pharmaceutically acceptable salting ion.

Preferably $R^3$ and $R^4$ both represent sodium.

The compound of formula (II) may suitably be administered by the parenteral route, preferably as a solution in sterile water or sterile isotonic saline B.P.

The following Example serves to illustrate the present invention; in the Example the compound: 6β-(2-carboxy-2-thien-3-yl acetamido)-6α-methoxy penicillanic acid, disodium salt is referred to by the reference number BRL 17421.

EXAMPLE

Human Volunteer Studies

Single dose studies. BRL 17421 was dosed by intramuscular injection (i.m.) to 25 healthy volunteers, including three females at the 1,000 mg dose level, and by intravenous (i.v.) injection to 18 healthy volunteers, including three females at the 1,000 mg dose level. All the volunteers participating in the reported studies were aged between 18 and 45 years and had passed a comprehensive medical examination during the previous 12 months and a complete haematological and clinical chemistry check prior to each study. Volunteers were fasted for up to 10 h and provided blood and urine samples immediately prior to dosing. Each volunteer was standardised with regard to food and fluid intake for the duration of the study. Volunteers with known penicillin hypersensitivities or had received medication up to seven days before the commencement of the study were excluded.

The doses were prepared from vials of sterile freeze-dried BRL 17421, containing either 250 mg or 500 mg as pure free acid (pfa), which was reconstituted in 2 ml volumes of sterile water B.P. for i.m. doses, or in 10 ml volumes or isotonic saline B.P. for i.v. doses. The 1,000 mg dose was reconstituted from two vials containing 500 mg BRL 17421 (pfa) and dissolved in 2 ml volumes of sterile water B.P. for i.m. administration and 20 ml sterile isotonic saline B.P. for i.v. dosage. The 2 ml i.m. dose was injected deep into the outer quadrant of the gluteus maximus and the i.v. administrations were given as a fast bolus injection of either 10 ml or 20 ml over 30 sec into the antecubital vein.

Figure 2:
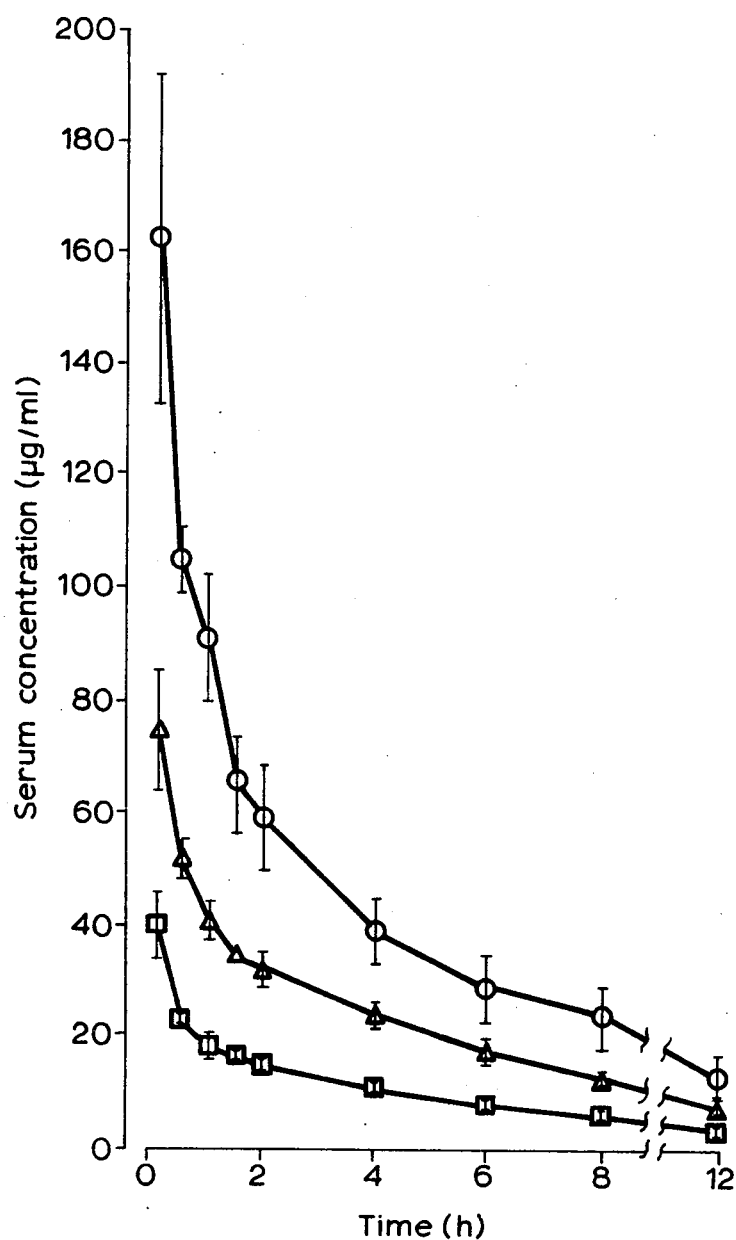

Mean serum concentrations of BRL 17421 following i.m. dosage are shown in FIG. 1, and after bolus i.v. injections in FIG. 2. A summary of some pharmacokinetic parameters derived after parenteral administration of BRL 17421 is given in Table 1. After single i.m. injections BRL 17421 gave high and prolonged serum levels with a terminal serum half-life which ranged between 5.0 and 5.4 h. The peak serum concentrations were reached approximately 2 h after dosing. A single i.m. injection of 500 mg gave a mean peak serum concentration of 48 μg/ml and levels in excess of 20 μg/ml were maintained for 8 h. Administration of a single 1,000 mg dose gave a mean peak serum concentration of 70 μg/ml approximately 2 h after dosing, with levels in excess of 18 μg/ml for 12 h.

Single i.v. bolus injections gave prolonged serum concentrations with a mean terminal serum half-life ranging between 4.3 and 4.6 h.

A single 1,000 mg dose gave serum concentrations in excess of 25 μg/ml for up to 6 h and a level of approx. 12 μg/ml 12 h after dosing. No antibiotic was detected in the serum 24 h after administration of the 1,000 mg dose by the i.v. route.

The urinary recoveries of unmetabolised BRL 17421 after both routes of administration was high, ranging from 72–82% after i.v. and 82–92% after i.m. administration.

No differences were observed between male and female subjects with respect to bioavailability and pharmacokinetics of the compound.

Repeat dose study. Two separate groups of three male volunteers were injected with 500 mg BRL 17421 (pfa) every 12 h for 3 days by the i.m. route into alternate sides of the gluteus maximus.

Figure 3:
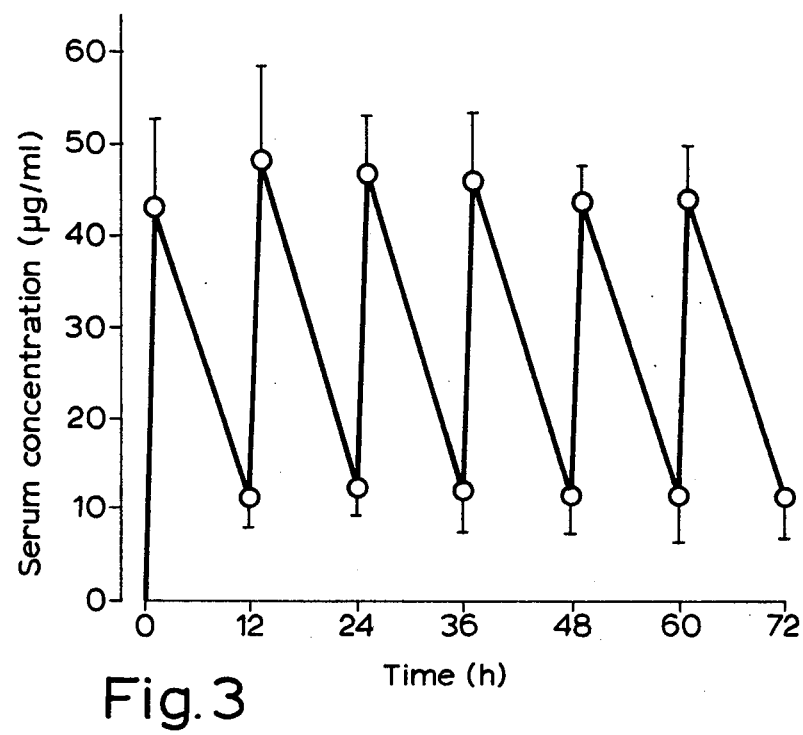

The serum concentrations achieved after repeated i.m. injections of a 500 mg dose, given every 12 h up to 72 h, are shown in FIG. 3. There was no evidence of accummulation of the drug after repeated administration over the period studied. The pharmacokinetic parameters given in Table 2 were similar and relatively constant following each injection over the period dosed.

Tolerance. Single and repeated i.m. injections of BRL 17421 were well tolerated, only mild transient pain being experienced after the 1,000 mg dose. The drug was also well tolerated by intravenous injection. No adverse drug-related abnormalities were observed after serum and urine analysis, or after haematological investigations. There was no evidence of clinically significant changes in either blood pressure or E.C.G. recordings performed on each volunteer during or after each study.

Microbiological assay. The concentrations of BRL 17421 (as pfa) in serum or urine were determined by microbiological assay using *P. aeruginosa* NCTC 10701 as the assay organism. The limit of detection of BRL 17421 in human serum was approximately 3 μg/ml. The sensitivity of the microbiological assay was generally increased two-fold by the incorporation of calcium chloride in the nutrient agar medium at a final concentration of 10 mM, allowing detection of BRL 17421 (pfa) at approximately 1.5 μg/ml in the presence of human serum.

Biochromatography of urine samples. Urine samples, collected over 0–2, 2–4, 4–6, 6–8 and 8–24 h periods after dosing, were applied to strips of chromatography paper (Whatman No. 1) and developed in a descending solvent system comprising; n-butanol, 4 parts; ethanol, 1 part; water, 5 parts (top phase) for 40 h. The tapes were removed, dried in warm air and placed onto nutrient agar plates seeded with either *N. catarrhalis* NCTC 3622 or *P. aeruginosa* NCTC 10701 and incubated at 37° C. for 18 h.

FIG. 1. Mean serum concentrations of BRL 17421 (± standard deviation following i.m. injection of 250 mg (□), 500 mg (Δ) or 1,000 mg (O) to groups of six subjects.

FIG. 2. Mean serum concentrations of BRL 17421 (± standard deviation) following i.v. injection of 250 mg (□), 500 mg (Δ) or 1,000 mg (O) to groups of six subjects.

FIG. 3. Mean serum concentration of BRL 17421 (± standard deviation) obtained 5 min before dosing and 1 h after dosing 500 mg i.m. at 0, 12, 24, 36, 48 and 60 h to six male subjects.

TABLE 1
Pharmacokinetic data derived after single parenteral dose of BRL 17421 to human volunteers[a]

| Route | Dose (mg) | Mean peak serum concentration (μg/ml) | Terminal half-life (h) | AUC (μg/ml per h) | Apparent volume of distribution (liters) | Urinary recovery 0–24 h | Urinary recovery 0–48 h | Renal clearance (ml/min) |
|---|---|---|---|---|---|---|---|---|
| i.m. | 250 | 25 | 5.0 | 193 | 9.3 | 86 | 91 | 19.7 |
|  | 500 | 48 | 5.2 | 405 | 9.3 | 87 | 92 | 19.0 |
|  | 1000 | 70 | 5.4 | 641 | 11.8 | 78 | 82 | 21.3 |
| i.v. | 250 | 40[b] | 4.3 | 139 | 11.4 | 80 | — | 24.2 |
|  | 500 | 74 | 4.6 | 303 | 11.0 | 82 | — | 22.5 |
|  | 1000 | 172 | 4.5 | 500 | 9.1 | 72 | — | 24.2 |

[a]Groups of six subjects
[b]Concentration 5 minutes after administration.

TABLE 2
Summary of pharmacokinetic data derived from intramuscular administration of 500 mg of BRL 17421 to six volunteers twice daily for 3 days

| Time period (h) | Terminal half-life (h) | AUC (μg/ml per h) | Urinary recovery Concentration (μg/ml) | Urinary recovery Amount excreted (mg) |
|---|---|---|---|---|
| 0–12 | 5.3 | 293 | 490 | 293 |
| 12–24 | 5.6 | 333 | 525 | 328 |
| 24–36 | 5.5 | 320 | 381 | 356 |
| 36–48 | 5.3 | 315 | 573 | 402 |
| 48–60 | 5.6 | 301 | 608 | 405 |
| 60–72 | 5.6 | 304 | 605 | 404 |
|  |  |  | Total excreted (mg): | 2263 |
|  |  |  | % total dose | 75 |

We claim:

1. A method of treating bacterial infections in humans which comprises parenterally administering to a human in need thereof one or two unit dosages, each of which comprises 1000 mg of a compound of the formula (II):

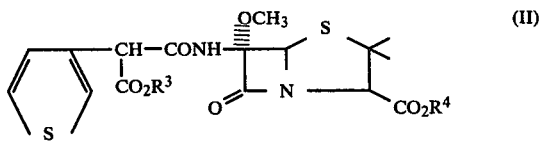

wherein $R^3$ and $R^4$ are both sodium, in combination with a pharmaceutically acceptable carrier.

2. A method according to claim 1 wherein one unit dosage per day is administered.

3. A method according to claim 1 wherein two unit dosages per day are administered.

4. A pharmaceutical composition in unit dosage form suitable for parenteral administration, useful for treating bacterial infections in humans, wherein each dosage unit contains 1000 mg of a compound of the formula (II):

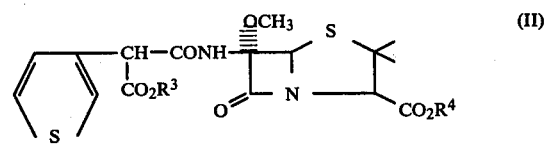

wherein $R^3$ and $R^4$ are both sodium, in combination with a pharmaceutically acceptable carrier.

* * * * *